(12) United States Patent
Chang et al.

(10) Patent No.: US 12,329,947 B2
(45) Date of Patent: Jun. 17, 2025

(54) MEDICAL INJECTION SYSTEM

(71) Applicant: SOLTEAM INCORPORATION, Taoyuan (TW)

(72) Inventors: Chun-Yun Chang, Taoyuan (TW); Yeong-Lii Lin, Taoyuan (TW); Chung-Yu Chen, Taoyuan (TW); Ping-Lung Lee, Taoyuan (TW); Frederic Delort, Taoyuan (TW)

(73) Assignee: SOLTEAM INCORPORATION, Taoyuan (TW)

( * ) Notice: Subject to any disclaimer, the term of this patent is extended or adjusted under 35 U.S.C. 154(b) by 814 days.

(21) Appl. No.: 17/586,068

(22) Filed: Jan. 27, 2022

(65) Prior Publication Data

US 2023/0233773 A1     Jul. 27, 2023

(51) Int. Cl.
| | |
|---|---|
| A61M 5/315 | (2006.01) |
| A61M 5/178 | (2006.01) |
| A61M 5/20 | (2006.01) |
| A61M 5/24 | (2006.01) |
| A61M 5/31 | (2006.01) |

(52) U.S. Cl.
CPC ........ *A61M 5/31568* (2013.01); *A61M 5/178* (2013.01); *A61M 5/20* (2013.01); *A61M 5/2422* (2013.01); *A61M 5/31* (2013.01); *A61M 5/31541* (2013.01); *A61M 5/31551* (2013.01); *A61M 5/31575* (2013.01); *A61M 5/31585* (2013.01); *A61M 5/31586* (2013.01); *A61M 2005/3126* (2013.01); *A61M 2205/581* (2013.01)

(58) Field of Classification Search
CPC .. A61M 5/31568; A61M 5/20; A61M 5/2422; A61M 5/31586; A61M 5/31541; A61M 5/31551; A61M 5/31575; A61M 5/31585; A61M 5/178; A61M 5/31; A61M 2005/3126; A61M 2205/581
See application file for complete search history.

(56) References Cited

U.S. PATENT DOCUMENTS

2021/0023309 A1*  1/2021  Chang ............... A61M 5/31585

FOREIGN PATENT DOCUMENTS

| | | |
|---|---|---|
| CN | 104582766 A | 4/2015 |
| CN | 109952121 A | 6/2019 |
| JP | 6717813 B2 | 7/2020 |
| JP | 2021006277 A | 1/2021 |
| TW | 202110499 A | 3/2021 |

* cited by examiner

*Primary Examiner* — Tasnim Mehjabin Ahmed
(74) *Attorney, Agent, or Firm* — ScienBiziP, P.C.

(57) ABSTRACT

A medical injection system is provided. The medical injection system comprises an injection module and the cartridge module coupled to the injection module. The injection module comprises a lead screw movable along an axial line into the cartridge module; a driver sleeve configured to partially accommodate the lead screw and to have a first sleeve end facing a distal end and having sleeve teeth; a dose plate including a first plate end facing the distal end, a second plate end facing a proximal end and having plate teeth corresponding to sleeve teeth, and a side surface located between the first plate end and the second plate end and having a surface tooth; and an indicia tube configured to accommodate the driver sleeve and the dose plate and to have tube concaves near a first tube end facing the distal end. The surface tooth corresponds to one of the tube concaves.

16 Claims, 16 Drawing Sheets

MEDICAL INJECTION SYSTEM

FIELD

The present disclosure generally relates to a medical injection system, particularly to a pen-shaped medical injection system for drug delivery.

BACKGROUND

Medical fluids or drug may be administered to a patient by an injection system. If frequent injections of the drug are deemed necessary for the patient, then the injection system should be portable and readily operable by the patient. Therefore, a portable medical injection system is commercially available for the patients who are in need of daily injections. A portable medical injection system typically has a shape of a pen.

The patient may use the portable medical injection system to administer a particular dose of the drug. For adjusting the dose, in a conventional pen-shaped injection system, the patient may need to visually check the dose of the drug that need to be administered. It may be difficult, especially for a visually-impaired patient, to check (or adjust) the dose of the drug for example, only ley seeing the dose marks on a conventional injection pen.

Therefore, there is a need for a non-visual dose-adjustment design for the medical injection system.

SUMMARY

In view of the shortcomings in the art, it is an objective of the present disclosure to provide a medical injection system having a drug cartridge.

It is also an objective of the present disclosure to provide a medical injection system with modular designs, whereby the modules can be examined and assembled separately, for example, during the manufacturing process.

It is also an objective of the present disclosure to provide a medical injection system that includes a dose plate. The dose plate is capable of generating different sounds when the medical injection system is moved (e.g., rotated in different directions).

A first aspect of the present disclosure provides a medical injection system, comprising: an injection module, and a cartridge module. The injection module comprises a lead screw movable along an axial line of the medical injection system; a driver configured to partially accommodate the lead screw and to be rotatable together with the lead screw; a driver sleeve configured to partially accommodate the driver and to have a first sleeve end facing a distal end of the medical injection system, the first sleeve end having a plurality of sleeve teeth; a dose plate including a first plate end facing the distal end, a second plate end facing a proximal end of the medical injection system, and a side surface located between the first plate end and the second plate end, the second plate end having a plurality of plate teeth corresponding to the plurality of sleeve teeth, the side surface having a surface tooth; and an indicia tube configured to accommodate the driver sleeve and the dose plate and to have a plurality of tube concaves near a first tube end facing the distal end, wherein the surface tooth of the dose plate corresponds to one of the plurality of tribe concaves. The cartridge module is coupled to the injection module and the lead screw is configured to move along the axial line into the cartridge module.

According to an embodiment of the first aspect, each of the plurality of the plate teeth is engaged with one of the plurality of sleeve teeth, and the surface tooth is engaged with one of the plurality of tube concaves.

According to another embodiment of the first aspect, the medical injection system further comprises a control knob rotatable in a first rotating, direction and a second rotating direction and coupled to the indicia tube, wherein when the control knob is rotated in the first rotating direction, each of the plurality of the plate teeth engaged with one of the plurality of sleeve teeth is rotated to engage with another one of the plurality of sleeve teeth, and when the control knob is rotated in the second rotating direction, the plurality of like concaves is rotated to change an engaged target of the surface tooth from one of the plurality of tube concaves to another one of the plurality of tube concaves.

According to another embodiment of the first aspect; a first sound is generated by the plurality of the plate teeth and the plurality of sleeve teeth for indicating the first rotating direction, and a second sound different from the first sound is generated by the surface tooth and the plurality of tube concaves for indicating the second rotating direction.

According to another embodiment of the first aspect, when the control knob is rotated in the first rotating direction, the indicia tube is moved toward the proximal end of the medical injection system, and when the control knob is rotated in the second rotating direction, the indicia tube is moved toward the distal end of the medical injection system.

According to another embodiment of the first aspect, the surface tooth includes a first inclined surface having a first slope and a second inclined surface having a second slope different from the first slope, the first inclined suit is configured to lock the surface tooth on the one of the plurality of tube concaves for rotating the dose plate in a third rotating direction by the indicia tube, and the surface tooth is moveable between the plurality of tube concaves through the second inclined surface without rotating the dose plate during a rotation of the indicia tube.

According to another embodiment of the first aspect, the surface tooth is locked on the one of the plurality of tube concaves to rotate the dose plate by the indicia tube when the control knob is rotated in the first rotating direction, and the surface tooth remains unrotated and the plurality of tube concaves is rotated by surrounding the surface tooth when the control knob is rotated in the second rotating direction.

According to another embodiment of the first aspect, the third rotating direction is identical to one of the first rotating direction and the second rotating direction.

According to another embodiment of the first aspect, when the control knob rotates the indicia tube in a first rotating direction, the dose plate is rotated by the indicia tube and the driver sleeve remains unrotated, and when the control knob rotates the indicia tube in a second rotating direction different from the first rotating direction, the dose plate and the driver sleeve remain unrotated.

According to another embodiment of the first aspect, when the control knob rotates the indicia tube in the first rotating direction, a first relative rotation between the dose plate and the indicia tube is caused to generate a first sound, and when the control knob rotates the indicia tube in the second rotating direction, a second relative rotation between the dose plate and the driver sleeve is caused to generate a second sound.

According to another embodiment of the first aspect, the medical injection system further comprises a screw nut engaged with the driver sleeve.

According to another embodiment of the first aspect, the driver sleeve further comprises a sleeve thread engaged with the screw nut, wherein the screw nut is rotatable over the sleeve thread; and a position structure located between the sleeve thread and the plurality of sleeve teeth and configured to define an initial position of the screw nut.

According to another embodiment of the first aspect, the position structure further comprises a position protrusion outwardly protruded near the sleeve thread; and a plurality of position notches coupled to the position protrusion, wherein the position protrusion is sandwiched between at least two of the plurality of position notches.

According to another embodiment of the first aspect, the screw nut further comprises a nut thread engaged with the sleeve thread to rotate the screw nut over the drive sleeve; and a nut recess engaged with the position protrusion for defining the initial position.

According to another embodiment of the first aspect, the indicia tube further comprises an internal protrusion surrounding an inner surface of the indicia tube and Heated near the first tube end, the internal protrusion is in contact with the first plate end of the dose plate and the dose plate is located between the internal protrusion and the second tube end facing the proximal end.

A second aspect of the present disclosure provides a medical injection system, comprising: an injection module, and a cartridge module. The injection module comprises a lead screw movable along an axial line of the medical injection system: a driver sleeve configured to partially accommodate the lead screw and to have a first sleeve end facing a distal end of the medical injection system, the first sleeve end having a plurality of sleeve teeth; a dose plate including a first plate end facing the distal end, a second plate end facing a proximal end of the medical injection system, and a side surface located between the first plate end and the second plate end, the second plate end having a plurality of plate teeth corresponding to the plurality of sleeve teeth, the side surface having a surface tooth; and an indicia tube configured to accommodate the driver sleeve and the dose plate and to have a plurality of tube concaves near a first tube end facing the distal end, the surface tooth of the dose plate corresponding to one of the plurality of tube concaves and including a first inclined surface having a first slope and a second inclined surface having a second slope different from the first slope. The cartridge module is coupled to the injection module, and the lead screw is configured to move along the axial line into the cartridge module.

BRIEF DESCRIPTION OF THE DRAWINGS

The present description will be better understood from the following detailed description read in light of the accompanying drawings, where.

DETAILED DESCRIPTION

Figure 1:
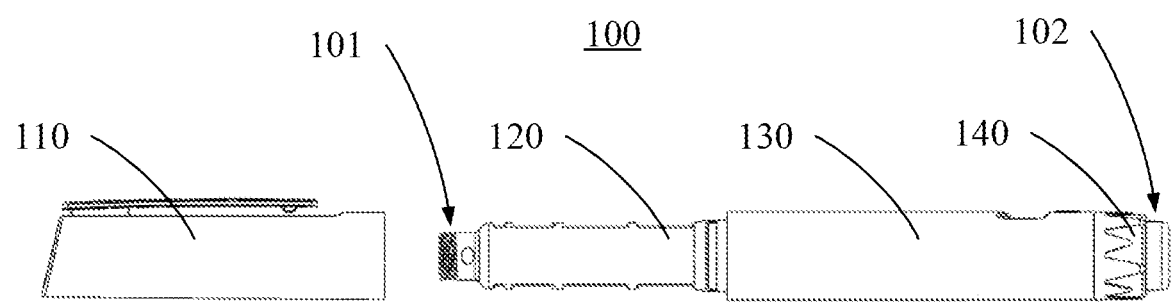
FIG. 1 is a diagram illustrating a perspective view of a medical injection system, in accordance with an embodiment of the present disclosure.

The following disclosure contains specific information pertaining to exemplary implementations in the present disclosure. The drawings in the present disclosure and their accompanying detailed disclosure are directed to merely exemplary implementations. However, the present disclosure is not limited to merely these exemplary implementations. Other variations and implementations of the present disclosure will occur to those skilled in the art Unless noted otherwise, like or corresponding elements among the figures may be indicated by like or corresponding reference numerals. Moreover, the drawings and illustrations in the present disclosure are generally not to scale and are not intended to correspond to actual relative dimensions.

For the purpose of consistency and ease of understanding, like features are identified (although, in some examples, not shown) by numerals in the exemplary figures. However, the features in different implementations may be differed in other respects, and thus shall not be narrowly confined to what is shown in the figures.

The disclosure uses the phrases "in one implementation," or "in some implementations," which may each refer to one or more of the same or different implementations. The term "coupled" is defined as connected, directly or indirectly through intervening components and is not necessarily limited to physical connections. The term "comprising" means "including, but not necessarily limited to"; it specifically indicates open-ended inclusion or membership in the so-described combination, group, series and the equivalent.

Additionally, for the purposes of explanation and non-limitation, specific details such as functional entities, techniques, protocols, standard, and the like are set forth for providing an understanding of the described technology. In other examples, detailed disclosure of well-known methods, technologies, system, architectures, and the like are omitted so as not to obscure the disclosure with unnecessary details.

The present disclosure is generally related to a medical injection system that includes a modular design anal a cartridge structure. The medical injection system may be used by a user to create a puncture on a person's (e.g., the same user or another patient's) skin and administer a drug or a medical fluid. In some implementations, the user may be an individual using the medical injection system of the present disclosure. In some implementations, the patient may be the same individual as the user or another individual who can be the subject of a drug administration performed by the medical injection system of the present disclosure. Since the medical injection system of the present disclosure can be operated by the same individual (e.g., the patient), the patient and the user described herein may be the same individual. In some implementations, the drug or the medical fluid may be administered by the medical injection system. In some implementations, an axial line may be regarded as an axis formed between two ends of a line in the medical injection system.

FIG. 1 is a diagram illustrating a perspective view of a medical injection system 100, in accordance with an embodiment of the present disclosure. The medical injection system 100 may include a cap 110, a cartridge module 120, a housing 130 and a button module 140.

On some implementations, the cap 110 is detachably coupled to the cartridge module 120 and is disposed on a distal end 101 of the medical injection system 100. In some implementations, the distal end 101 may be one of two ends of the medical injection system 100 which is directed toward a puncture site of the patient's skin while using the medical injection system 100. In some implementations, the distal end 101 of the medical injection system 100 may be one of two ends of the cap 110 when the cap 110 covers the cartridge module 120. In some implementations, the cartridge module 120 may further include a plurality of cartridge components integrated together to form the cartridge module 120, in some implementations, at least one of the cartridge components in the cartridge module 120 may be detachably coupled to the other cartridge components in the cartridge module 120. The cartridge module 120 may contain a drug or a medical fluid.

In some implementations, the housing 130 may be disposed on a proximal end 102 relative to the cartridge module 120 of the medical injection system 100, in some implementations, the proximal end 102 may be the other one of the two ends of the medical injection system 100 which is opposite to the distal end 101 while using the medical injection system 100. In some implementations, the button module 140 may further, include a plurality of button components integrated together to generate the button module 140. In some implementations, at least one of the button components in the button module 140 may be detachably coupled to the other button components in the button module 140. In some implementations, the button module 140 may be operated as a button (e.g., may be capable of being pushed/pressed by the user).

In some implementations, a pan of the cartridge module 120 may be partially accommodated in the housing 130. In some implementations, one or more of the cartridge components may be partially or completely covered by the housing 130, while the other cartridge components may not be covered by the housing 130.

In some implementations, a part of the button module 140 may be partially accommodated in the housing 130. In some implementations, one or more of the button components may be partially or completely covered by the housing 130, while the other button components may not be covered by the housing 130. In another implementations, each of the button components may be partially covered by the housing 130. In other implementations, all of the button components may be completely covered by the housing 130.

Figure 2:
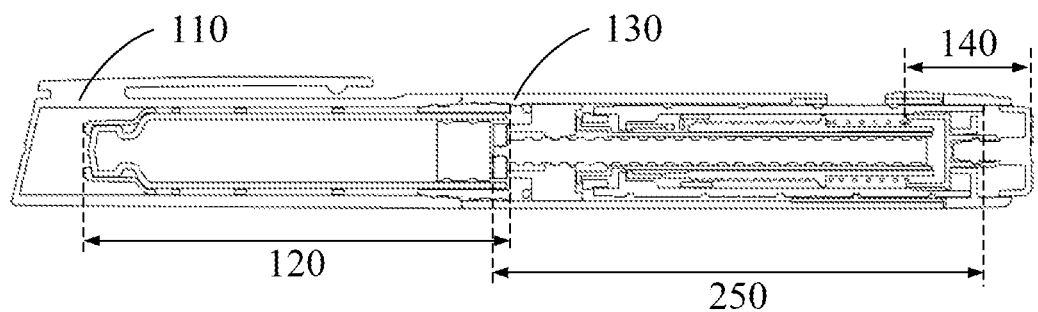
FIG. 2 is a cross-sectional view of the medical injection system, in accordance with an embodiment of the present disclosure.

FIG. 2 is a cross-sectional view of the medical injection system 100, in accordance with an embodiment of the present disclosure. The medical injection system 100 may include the cap 110, the cartridge module 120, the housing 130, the button module 140, and may further include an injection module 250.

In some implementations, the housing 130 may accommodate the injection module 250. With further reference to FIG. 1, the injection module 250 used to inject the drug or the medical fluids may be disposed on the proximal end 102 of the medical injection system 100. In some implementations, the injection module 250 may further include a plurality of injection components it together to generate the injection module 250. In some implementations, at least one of the injection components in the injection module 250 may be detachably coupled to the other injection components in the injection module 250. In some implementations, the injection module 250 may be detachably coupled to the cartridge module 120. In some implementations, at least one of the injection components may be inserted into the cartridge module 120.

Figure 3:
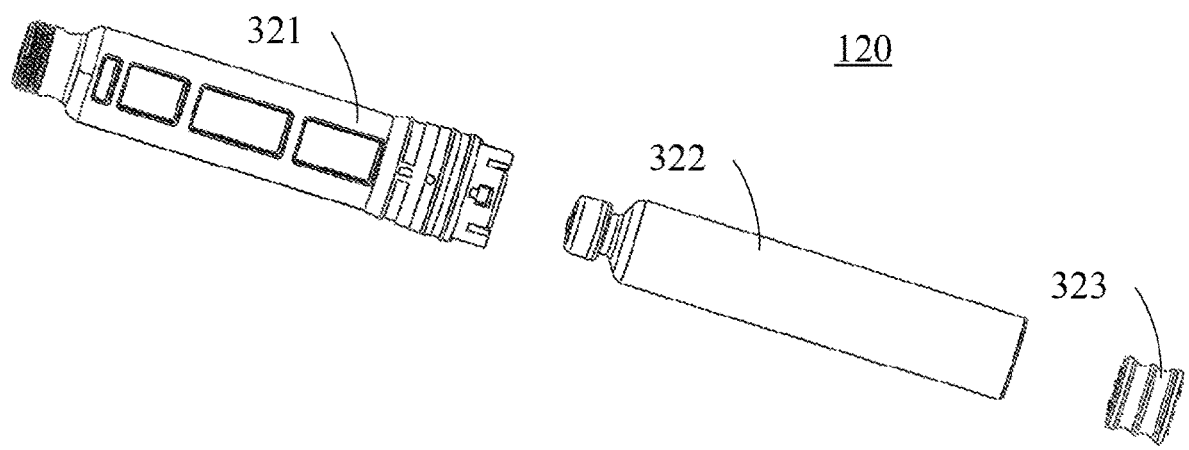
FIG. 3 is an exploded view of a cartridge module of the medical injection system, in accordance with an embodiment of the present disclosure.

FIG. 3 is an exploded view of a cartridge module 120 of the medical injection system, in accordance with an embodiment of the present disclosure. The cartridge module 120 may further include a cartridge holder 321, a cartridge device 322 and a stopper 323.

In some implementations, the cartridge holder 321 may accommodate the cartridge device 322. The cartridge device 322 may be detachably fixed by the cartridge holder 321. The drug or the medical fluid may be contained in the cartridge device 322. With further reference to FIG. 2, the stopper 323 may be disposed in the cartridge device 322 for being pushed by the injection module 250. In some implementations, there may be a hollow needle (not shown) coupled to the cartridge holder 321 for puncturing the skin of the patient and delivering the drug or the medical fluid contained in the cartridge device 327.

Figure 4:
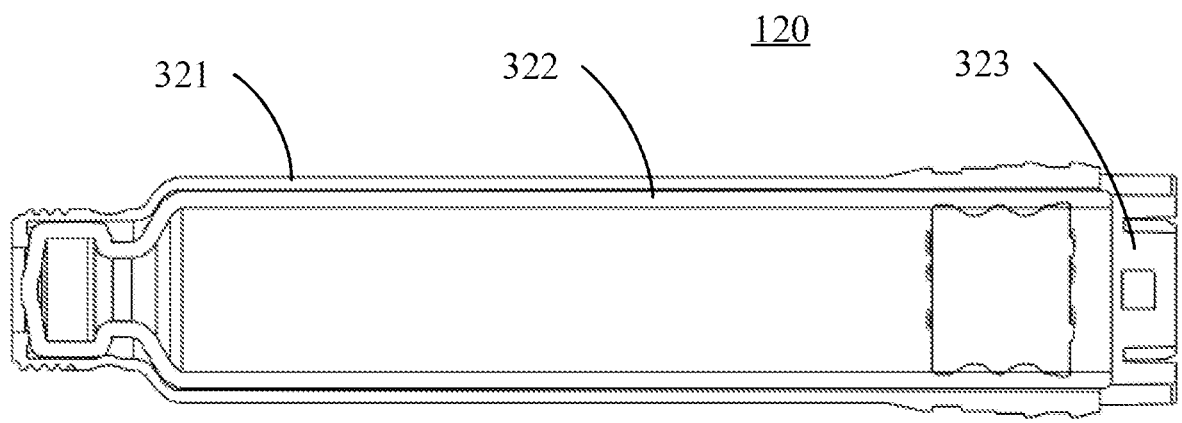
FIG. 4 is a cross-sectional view of the cartridge module, in accordance with an embodiment of the present disclosure.

FIG. 4 is a cross-sectional view of the cartridge module 120, in accordance with an embodiment of the present disclosure. The direction of the cross-sectional view shown in FIG. 4 may be different from the direction of the cross-sectional view shown in FIG. 2. Thus, the structure of the cartridge module 120 shown in FIG. 4 may be slightly different from what is shown in FIG. 2. With reference to FIG. 2, in some implementations, each of the cartridge components including the cartridge holder 321, the cartridge device 322 and the stopper 323 may be partially covered by the housing 130.

In some implementations, with reference to FIG. 4, the cartridge device 322 it ay be loaded into the cartridge holder 321 and the stopper 323 may be disposed in the cartridge device 322 for defining a volume of the drug or the medical fluid contained in the cartridge device 322. With further reference to FIG. 1, when the stopper 323 is pushed to move toward the distal end 101 of the medical injection system 100, the volume of the drug or the medical fluid contained in the cartridge device 322 may be reduced. Thus, the drug or the medical fluid stored in the cartridge device 322 may be extruded from a hollow needle (not shown) by the stopper 323.

Figure 5:
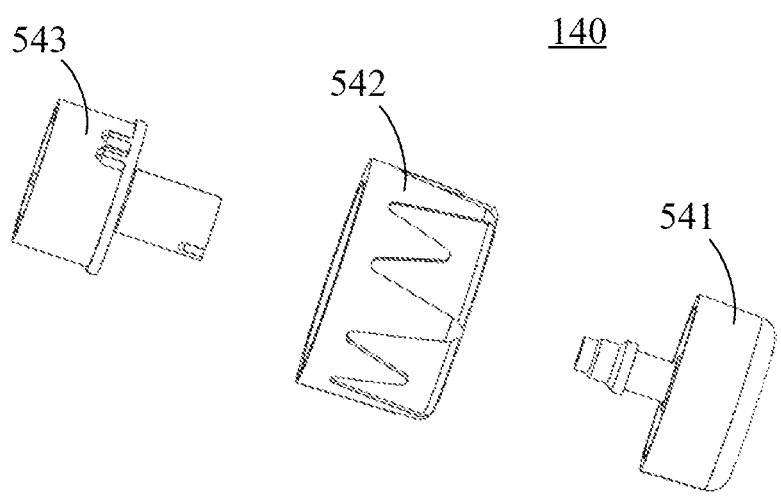
FIG. 5 is an exploded view of a button module of the medical injection system, in accordance with an embodiment of the present disclosure.

FIG. 5 is an exploded view of a button module 140 of the medical injection system, in accordance with an embodiment of the present disclosure. The button module 140 may further include a control button 541, a control knob 542 and a sleeve holder 543.

In some implementations, the control knob 542 may partially accommodate the control button 541 and the sleeve holder 543. With further reference to FIG. 5, the control button 541 may be engaged with the sleeve holder 543, and the control knob 542 may be sandwiched between the control button 541 and the sleeve holder 543.

Figure 6:
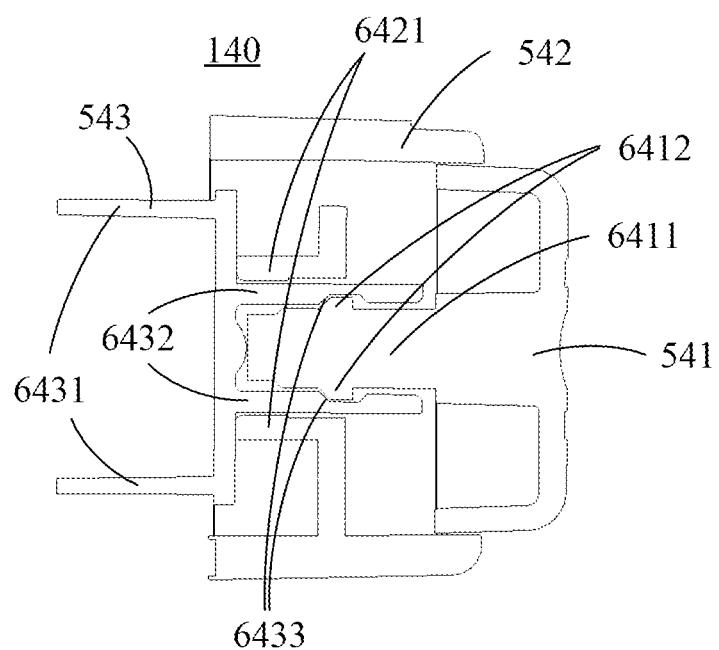
FIG. 6 is a cross-sectional view of the button module, in accordance with an embodiment of the present disclosure.

FIG. 6 is a cross-sectional view of the button module 140, in accordance with an embodiment of the present disclosure. The direction of the cross-sectional view shown in FIG. 6 may be different from the direction of the cross-sectional view shown in FIG. 2, Thus, the structure of the button module 140 shown in FIG. 6 may be slightly different from what is shown in FIG. 2.

In some implementations, the control button 541 may further include a button connection 6411 and a button protrusion 6412 protruded from the button connection 6411. In some implementations, the control knob 542 may further include a knob passage 6421. In some implementations, the sleeve holder 543 may further include a first holder connection 6431, a second holder connection 6432 and a holder recess 6433 located at the second holder connection 6432.

In some implementations, the button connection 6411 of the control button 541 may be coupled to the second holder connection 6432 by engaging the button protrusion 6412 with the holder recess 6433. In some implementations, the engagement between the button protrusion 6412 and the holder recess 6433 may be penetrated through the knob passage 6421, such that the control knob 542 may also be coupled to the control button 541 and the sleeve holder 543.

Figure 7:
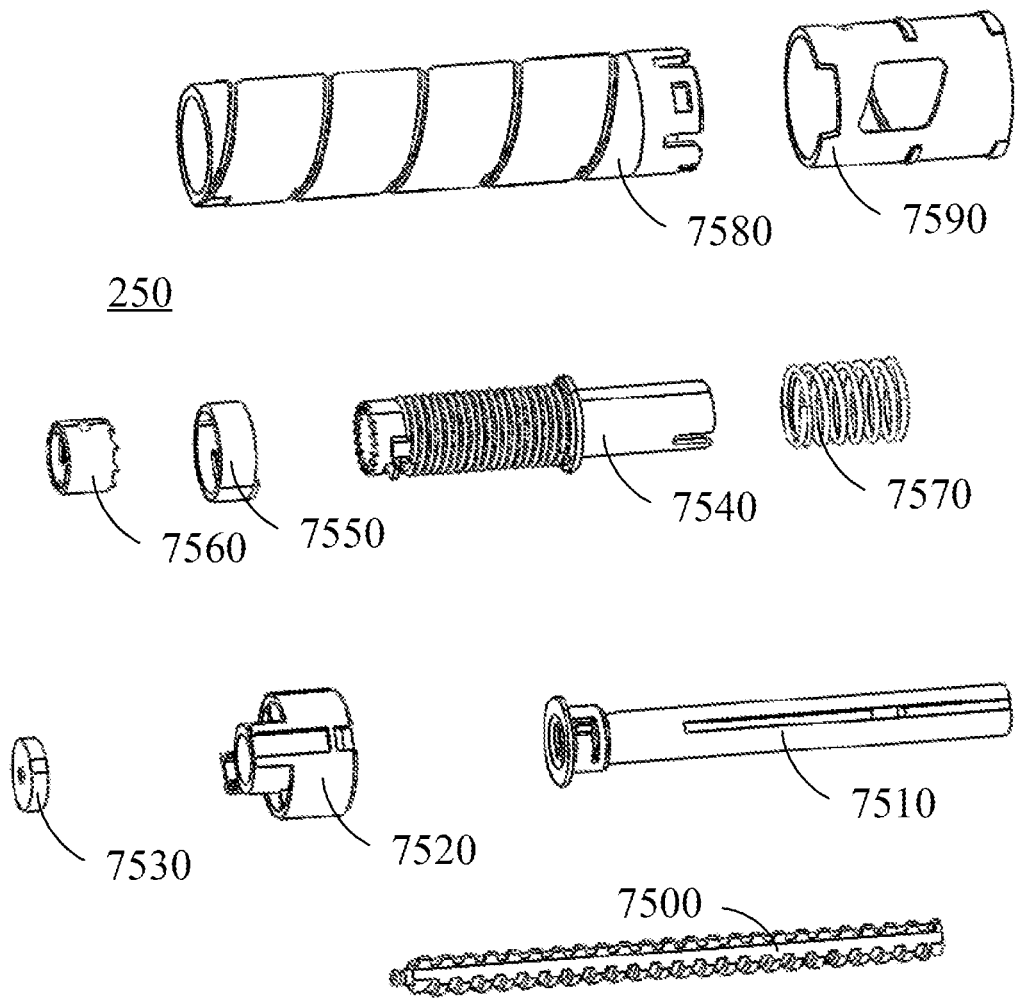
FIG. 7 is an exploded view of an injection module of the medical injection system, in accordance with an embodiment of the present disclosure.

FIG. 7 is an exploded view of an injection module 250 of the medical injection system, in accordance with an embodiment of the present disclosure. The injection module 250 may further include a lead screw 7500, a driver 7510, a locking nut 7520, a rotating ring 7530, a driver sleeve 7540, a screw nut 7550, a dose plate 7560, a button spring 7570, an indicia tube 7580, and a thread insert 7590.

In some implementations, the lead screw 7500, the driver 7510, the driver sleeve 7540, and the indicia tube 7580 may be generally assembled concentrically with each other. In some implementations, the lead screw 7500 is the innermost component among the lead screw 7500, the driver 7510, the driver sleeve 7540, and the indicia tube 7580. In some implementations, the lead screw 7500 may be movable along the axial line of the medical in system 100. With further reference to FIG. 2, the cartridge module 120 may be coupled to the injection module 250, and, the lead screw 7500 may move along the axial line to insert into the cartridge module 120.

In some implementations, the driver 7510 may be coupled to the locking nut 7520 and the locking nut 7520 may be further coupled to the rotating ring 7530. In other words, the locking nut 7520 may be located, and sandwiched, between the driver 7510 and the rotating ring 7530. In some implementations, the driver 7510 may partially accommodate the lead screw 7500 and be rotatable together with the lead screw 7500.

In some implementations, the driver sleeve 7540 may partially accommodate the driver 7510. With further reference to FIG. 7, in some implementations, the button spring 7570 may cover the driver sleeve 7540 at a proximal end 102 of the driver sleeve 7540. In some implementations, the screw nut 7550 may cover the driver sleeve 7540 at a distal end of the driver sleeve 7540. In some implementations, the dose plate 7560 may be coupled to the driver sleeve 7540 by coupling a proximal end of the dose plate 7560 with the distal end of the driver sleeve 7540. In addition, in some implementations, the thread insert 7590 may cover the indicia tube 7580, while the indicia tube 7580 may accommodate the driver sleeve 7540.

Figure 8:
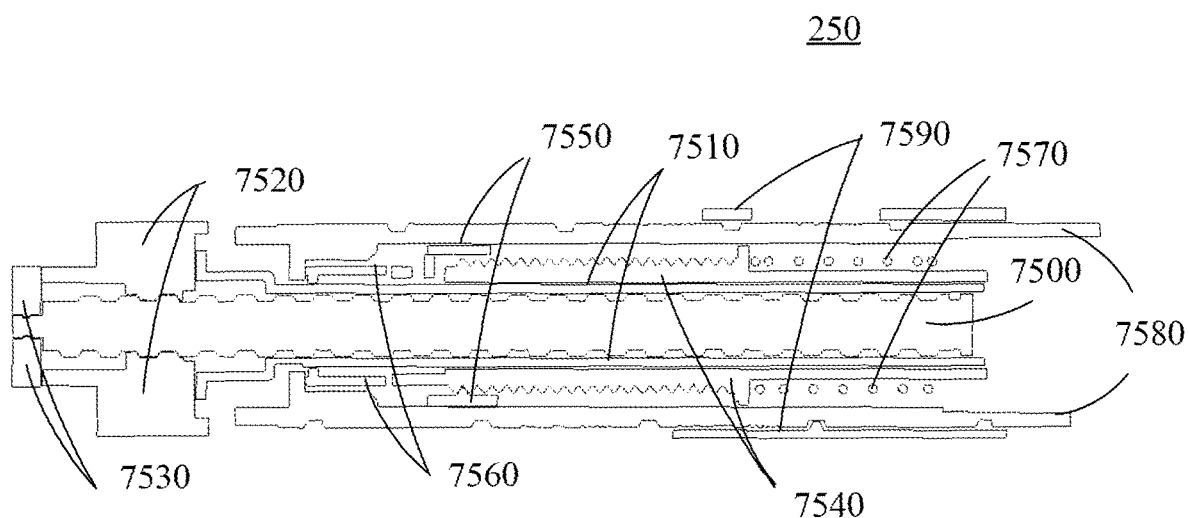
FIG. 8 is a cross-sectional view of the injection module, in accordance with an embodiment of the present disclosure.

FIG. 8 is a cross-sectional view of the injection module 250, in accordance with an embodiment of the present disclosure. The direction of the cross-sectional view shown in FIG. 8 may be different from the direction of the cross-sectional view show in FIG. 2. Thus, the structure of the injection module 250 shown in FIG. 8 may be slightly different from what is shown in FIG. 2. Specifically, FIG. 8 illustrates the combination of the lead screw 7500, the drivel 7510, the locking nut 7520, the rotating ring 7530 the driver sleeve 7540, the screw nut 7550, the dose plate 7560, the button spring 7570, the indicia tube 7580, and the thread insert 7590.

In some implementations, the locking, nut 7520 and the rotating ring 7530 may be coupled to each other. In some implementations, the lead screw 7500 may penetrate through the locking nut 7520 and the rotating ring 7530, and the locking nut 7520 and the rotating ring 7530 may cover the lead screw 7500. In some implementations, a tip of the lead screw 7500 (e.g., at a distal end of the lead screw 7500) may be coplanar with a surface of the rotating ring 7530 (e.g., at a distal end of the rotating ring 7530). With further reference to FIG. 2, when the lead screw 7500 is moved toward the cartridge module 120, the rotating ring 7530 may also be moved toward the cartridge module 120.

In some implementations, the driver 7510 may be exposed from the indicia tube 7580 and abutted against the locking nut 7520. Thus, the driver 7510 may be partially accommodated by the indicia tube 7580. In some implementations, the driver 7510 may penetrate through the driver sleeve 7540, the screw nut 7550 and the dose plate 7560. In addition, the dose plate 7560 may be abutted against the indicia tube 7580 at a distal end of the dose plate 7560. As such, in some implementations, there may be no relative displacement between the dose plate 7560 and the indicia tube 7560 along the axial line of the medical injection system 100.

In some implementations, the indicia tube 7580 may completely accommodate the driver sleeve 7540, the screw nut 7550, the dose plate 7560, the button spring 7570 and may partially accommodate the driver 7510 and the lead screw 7500. In some implementations, the thread insert 7590 may partially accommodate the indicia tube 7580.

Figure 9:
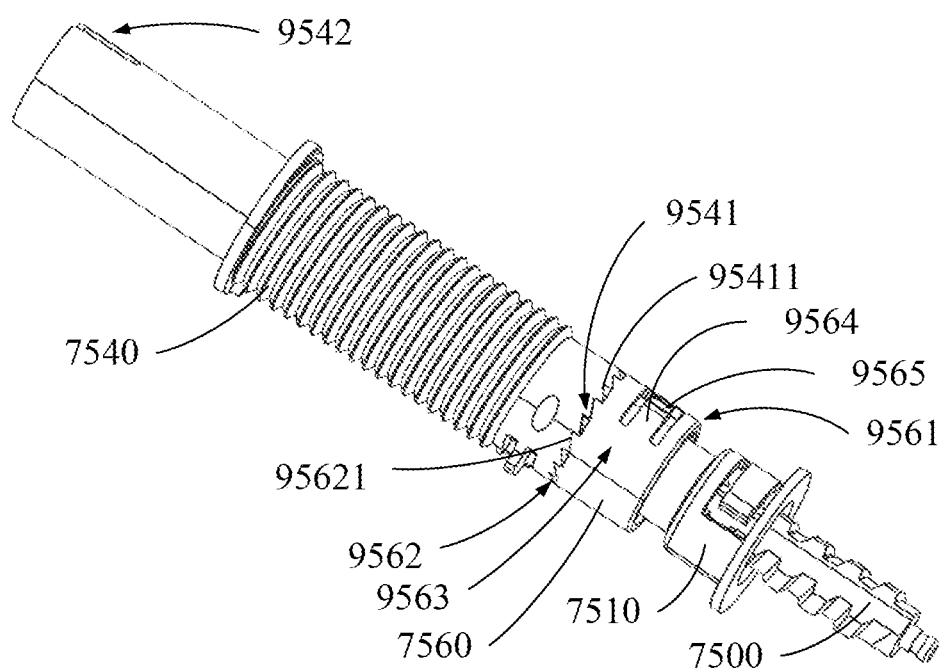
FIG. 9 is a perspective view of a combination of the lead screw, the driver, the driver sleeve, and the driver plate of the medical injection system, in accordance with an embodiment of the present disclosure.

FIG. 9 is a perspective view of a combination of the lead screw 7500, the driver 7510, the driver sleeve 7540 and the dose plate 7560 of the medical injection system, in accordance with an embodiment of the present disclosure. With further reference to FIG. 1, in some implementations, the driver sleeve 7540 may include a first sleeve end 9541 facing the distal end 101 of the medical injection system 100 and a second sleeve end 9542 facing, the proximal end 102 of the medical it system 100. In some implementations, the dose plate 7560 may include a first plate end 9561 facing the distal end 101 of the medical injection system 100, a second plate end 9562 facing the proximal end 102 of the medical injection system 100, and a side surface 9563 located between the first plate end 9561 and the second plate end 9562.

In some implementations, the first sleeve end 9541 may further include a plurality of sleeve teeth 95411. In addition, the second plate end 9562 may also include a plurality of plate teeth 95621 corresponding to the sleeve teeth 95411. In some implementations, each of the plate teeth 95621 may correspond to one of the sleeve teeth 95411 when the number of the plate teeth 95621 is less than or equal to the number of the sleeve teeth 95411. In some implementations, each of the sleeve teeth 95411 may correspond to one of the plate teeth 95621 when the number of the plate teeth 95621 is greater than or equal to the number of the sleeve teeth 95411. In some implementations, the side surface 9563 may further include a flexible plate 9564 and a surface tooth 9565 protruded from the flexible plate 9564.

Figure 10:
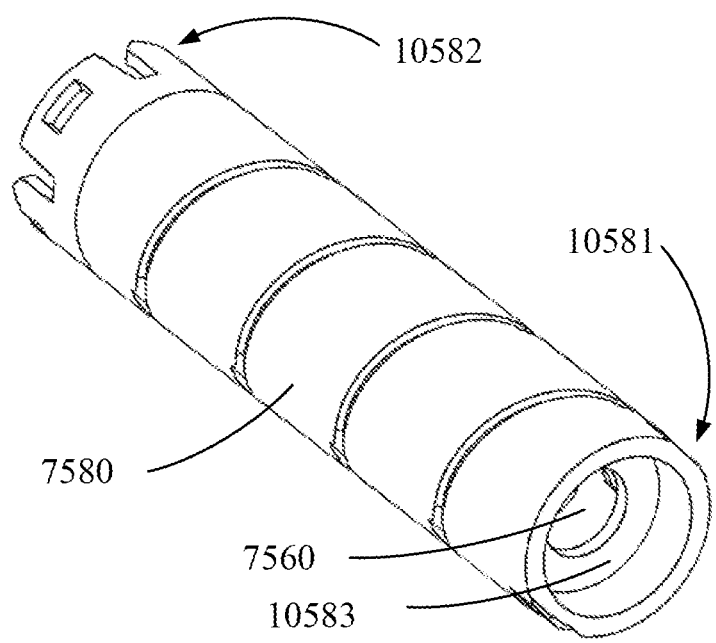
FIG. 10 is a perspective view of a combination of the driver plate and the indicia tube of the medical injection system, in accordance with an embodiment of the present disclosure.

FIG. 10 is a perspective view of a combination of dose plate 7560 and the indicia tube 7580 of the medical injection system, in accordance with an embodiment of the present disclosure. In some implementations, the indicia tube 7580 may completely accommodate the dose plate 7560. With further reference to FIG. 1, in some implementations, the indicia tube 7580 may include a first tube end 10581 facing the distal end 101 of the medical injection system 100 and a second tube end 10582 facing the proximal end 102 of the medical injection system 100.

In some implementations, the indicia tube 7580 may further include an internal protrusion 10583. In some implementations, the internal protrusion 10583 may inwardly surround an inner surface (not shown) of the indicia tube 7580 and may be located near the first tube end 10581. With further reference to FIG. 9, in some implementations, the internal protrusion 10583 may be in contact with the first plate end 9561 of the dose plate 7560. Thus, the dose plate 7560 may be located between the internal protrusion 10583 and the second tube end 10582 and may be sandwiched between the internal protrusion 10583 and the first sleeve end 9541 of the driver sleeve 7540.

Figure 11:
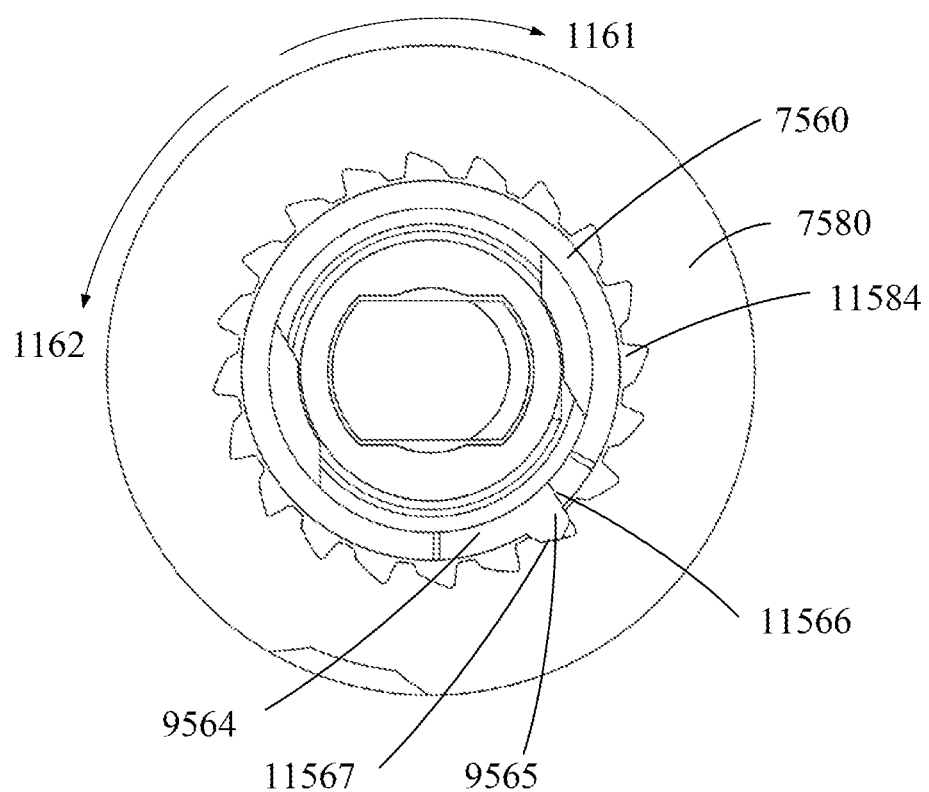
FIG. 11 is a cross-sectional view of a combination of the dose plate and the indicia tube of the medical injection system, in accordance with an embodiment of the present disclosure.

FIG. 11 is a cross-sectional view of a combination of the dose plate 7560 and the indicia tube 7580 of the medical injection system, in accordance with an embodiment of the present disclosure. In some implementations, the indicia tube 7580 may include a plurality of tube concaves 11584.

In some implementations, the tube concaves 11584 may an surround the inner surface of the indicia tube 7580. In some implementations, the surface tooth 9565 of the dose plate 7560 may correspond to one of the tube concaves 11584. In some implementations, the surface tooth 9565 may engage with one of the tube concaves 11584. Thus, with further reference to FIG. 9 and FIG. 10, the tube concaves 11584 may be located near the first tube end 10581 and between the internal protrusion 10583 and the first sleeve end 9541 of the driver sleeve 7540.

In some implementations, the surface tooth 9565 may further include a first inclined surface 11566 having a first slope and a second inclined surface 11567 having a second slope (e.g., that is different from the first slope). The first slope and the second slope may be calculated based on the flexible plate 9564. Thus, the second slope may be less than the first slope. In some implementations, each of the tube concaves 11584 may further include a third inclined surface (not shown) that has a third slope and a fourth inclined surface (not shown) that has a fourth slope. In some implementations, the third slope may be similar to the first slope and the fourth slope may be similar to the second slope. Thus, the surface tooth 9565 may engage closely with one of the tube concaves 11584.

In some implementations, the indicia tube 7580 may be rotatable in a first rotating direction 1161 and a second rotating direction 1162. In some implementations, when the indicia tube 7580 rotates in the first rotating direction 1161, the tube concaves 11584 may also rotate in the first rotating direction 1161. In some implementations, the third inclined surface of the tube concaves 11584 may be abutted against the first inclined surface 11566 of the surface tooth 9565. Thus, the dose plate 7560 may be rotated in a third rotating direction by the indicia tube 7580 since the first slope and the third slope are high enough for the third inclined surface to push the first inclined surface 11566 to be rotated without generating a slide between the first inclined surface 11566 and the third inclined surface. More specifically, an engagement between the first inclined surface 11566 and the third inclined surface may lock the surface tooth 9565 of the dose plate 7560 on the tube concaves 11584 of the indicia tube 7580 for rotating the dose plate 7560 in the third rotating direction. In some implementations, the third rotating direction of the dose plate 7560 may be identical to the first rotating direction 1161 of the indicia tube 7580. In some implementations, the third rotating direction of the dose plate 7560 may be identical to the second rotating direction 1162 of the indicia tube 7580, for example, when the second slope is enough to prevent a slide between the second inclined surface 11567 and the fourth inclined surface.

In some implementations, when the indicia tube 7580 rotates in the second rotating direction 1162 the tube concaves 11584 may also rotate in the second rotating direction 1162. In some implementations, the fourth inclined surface of the tube concaves 11584 may be abutted against the second inclined surface 11567 of the surface tooth 9565, However, the second slope and the fourth slope may be low enough for the fourth inclined surface to press the second inclined surface 11567 down. Thus, the dose plate 7560 may not be rotated in the second rotating direction 1142 by the indicia tube 7580 since a slide between the second inclined surface 11567 and the fourth inclined surface may be induced due to the low slope. In other words, the surface tooth 9565 may be moveable between the plurality of tube concaves 11584 through the second inclined surface 11567 without rotating the dose plate 7560 when the indicia tube 7580 rotates in the second rotating direction 1162.

Figure 12:
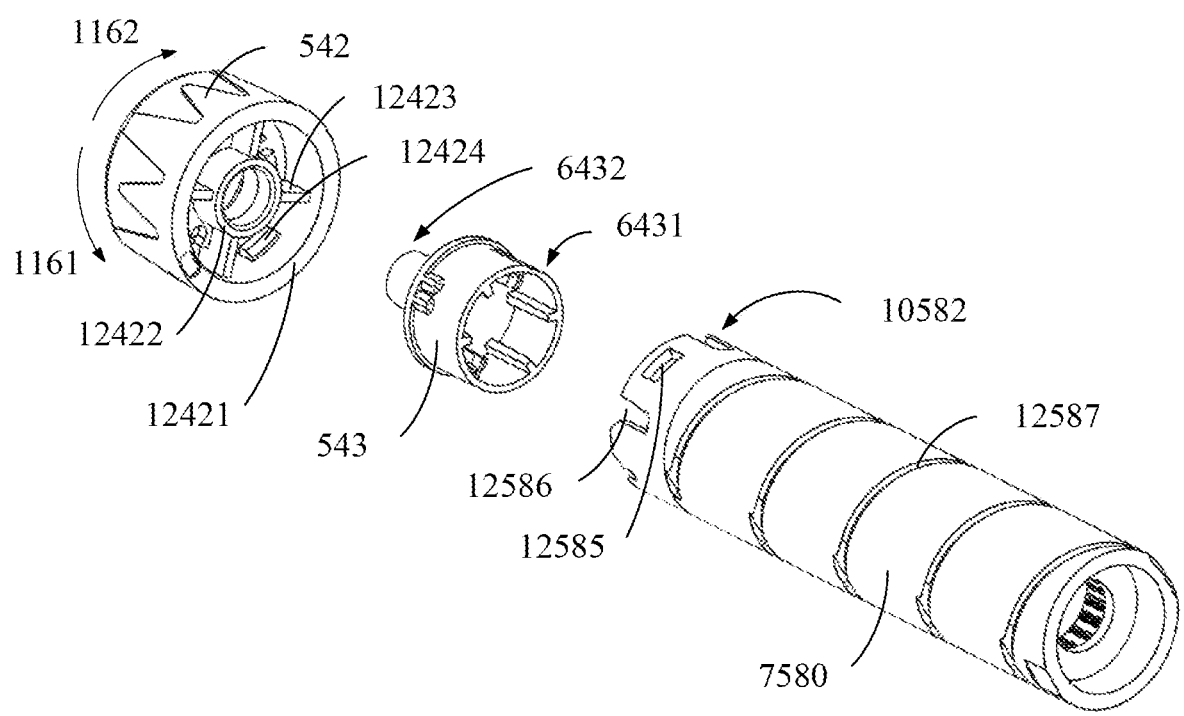
FIG. 12 is a perspective view of a combination of the control knob, the sleeve bolder, and the indicia tube of the medical injection system, in accordance with an embodiment of the present disclosure.

FIG. 12 is a perspective view of a combination of the control knob 542, the sleeve holder 543 and the indicia tube 7580 of the medical injection system, in accordance with an embodiment of the present disclosure. In some implementations, the control knob 542 may include an outer ring 12421, an inner ring 12422 located at a center of the outer ring 12421, a plurality of knob bridges 12423 connecting the outer ring 12421 to the inner ring 12422, and a knob protrusion 12424 inwardly protruded from an inner surface of the outer ring 12421. With further reference to FIG. 1 and FIG. 6, the sleeve holder 543 may include a first holder connection 6431 inserted into the second tube end 10582 and facing the distal end 101 and a second holder connection 6432 inserted into the inner ring 12422 and facing the proximal end 102. In some implementations, the second tube end 10582 may further include a tube lock 12585 and a plurality of tube recesses 12586. In some implementations, the indicia tube 7580 may further include a tube thread 12587 located at an outer surface of the indicia tube 7580.

Figure 13:
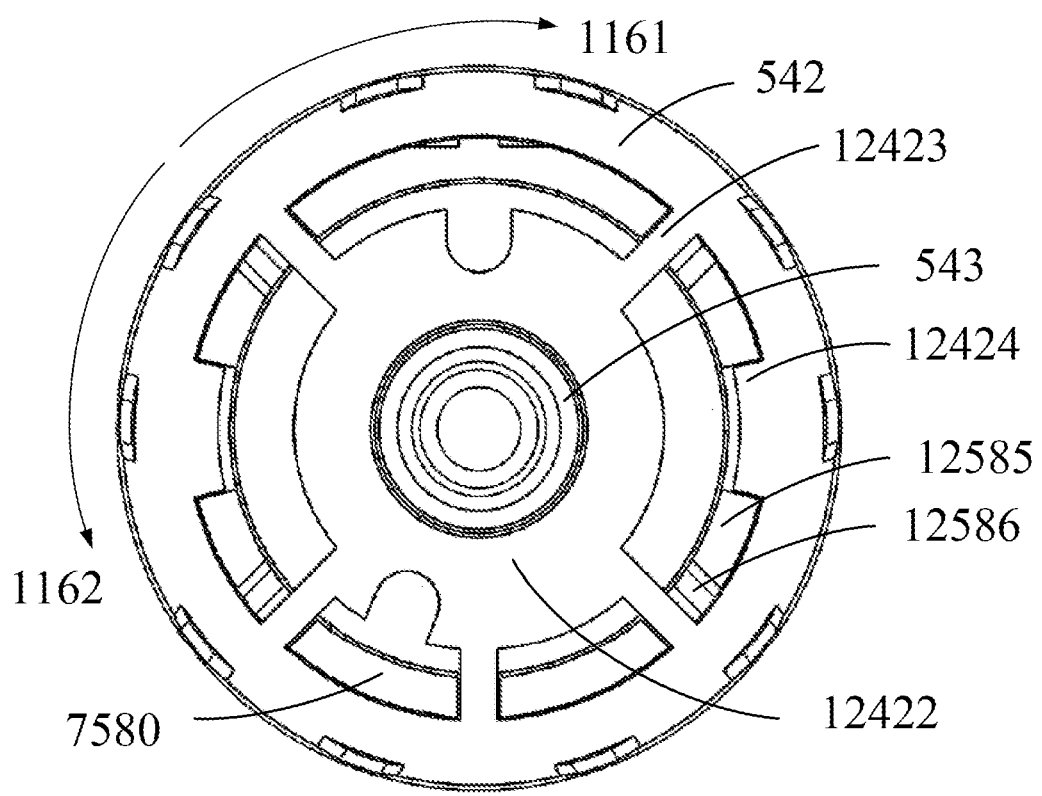
FIG. 13 is a cross sectional view of a combination of the control knob, the sleeve holder, and the indicia tube of the medical injection system, in accordance with an embodiment of the present disclosure.

FIG. 13 is a cross sectional view of a combination of the control knob 542, the sleeve holder 543 and the indicia tube 7580 of the medical injection system, in accordance with an embodiment of the present disclosure.

In some implementations, the knob bridges 12423 of the control knob 542 may be engaged with the tube recesses 12586 of the indicia tube 7580 and the knob protrusion 12424 of the control knob 542 may be engaged with the tube lock 12585 of the indicia tube 7580 when the control knob 542 is coupled to the indicia tube 7580. Thus, when the control knob 542 is rotated in one of the first rotating direction 1161 and the second rotating direction 1162 (e.g., by a user), the indicia tube 7580 may also be rotated in the one of the first rotating direction 1161 and, the second rotating direction 1162 by the control knob 542 due to an engagement between the knob protrusion 12424 of the control knob 542 and the tube lock 12585 of the indicia tube 7580.

In some implementations, an inner surface of the inner ring 12422 may be smooth (e.g., without any protrusion and/or recess). Thus, when the control knob 542 is rotated in one of the first rotating direction 1161 and the second rotating direction 1162 by user, the sleeve holder 543 may remain unrotated due to no engagement between the control knob 542 and the sleeve holder 543.

In some implementations, the control knob 542 may be rotatable in the first rotating direction 1161 and the second rotating direction 1162. In some implementations, when the control knob 542 is rotated in the first rotating direction 1161 by a user, the indicia tube 7580 may also be rotated in the first rotating direction 1161 by the control knob 542. With further reference to FIG. 11, the surface tooth 9565 is locked on one of the tube concaves 11584 to rotate the dose plate 7560 by the indicia tube 7580 when the control knob 542 is rotated in the first rotating direction 1161. With further reference to FIG. 9, each of the plurality of the plate teeth 95621 engaged with one of the sleeve teeth 95411 may also be rotated to engage with another one of the sleeve teeth 95411 when the control knob 542, the indicia tube 7580 and the dose plate 7560 are rotated in the first rotating direction 1161. In some implementations, the driver sleeve 7540 may remain unrotated since the sleeve holder 543 remains unrotated. Thus, a first relative rotation between the dose plate 7560 and the indicia tube 7580 may be generated. In addition, with reference to FIG. 8, the button spring 7570 may keep pushing the driver sleeve 7540 such that the driver sleeve 7540 may be abutted against the dose plate 7560 by the button spring 7570. A first sound (e.g., a voice) may be generated by the plate teeth 95621 and the sleeve teeth 95411 for indicating, the first rotating direction 1161 when the button spring 7570 pushes the sleeve teeth 95411 to hit the rotating plate teeth 95621.

In some implementations, when the control knob 542 is rotated in the second rotating direction 1162 by a user, the indicia tube 7580 may also be rotated in the second rotating direction 1162 by the control knob 542. With reference to FIG. 11, the surface tooth 9565 may remain unrotated and the tube concaves 11584 may be rotated to circle around the surface tooth 9565 when the control knob 542 is rotated in the second rotating direction 1162. With further reference to FIG. 9, the tube concaves 11584 may be rotated to change an engaged target of the surface tooth 9565 from one of the tube concaves 11584 to another one of the tube concaves 11584 when the control knob 542 and the indicia tube 7580 are rotated in the second rotating direction 1162. In some implementations, the dose plate 7560 and the driver sleeve 7540 may remain unrotated since the sleeve holder 543 remains unrotated. Thus, a second relative rotation between the dose plate 7560 and the driver sleeve 7540 may be generated. In addition, the flexible plate 9564 may be flexible enough to press the surface tooth 9565 back into one of the tube concaves 11584, such that the surface tooth 9565 may keep engaging with the tube concaves 11584 by the flexible plate 9564. A second sound (e.g., a different voice) different from the first sound may be generated by the surface tooth 9565 and the tube concaves 11584 for indicating the second rotation direction 1162 when the flexible plate 9564 presses the surface tooth 9565 to hit the tube concaves 11584.

In some implementations, the thread insert 7590 may include an inward screw located at an inner surface of the thread insert 7590. With reference to FIG. 11, in some implementations, the inward screw of the thread insert 7590 may engage with the tube thread 12587, In some implementations, when the control knob 542 is rotated in the first rotating direction 1161, the indicia tube 7580 may also be rotated in the first rotating direction 1161 and may be moved toward the proximal end 102 (e.g., as shown in FIG. 1) of the medical injection system 100 based on a first thread direction. In some implementations, when the control knob 542 is rotated in the second rotating direction 1162, the indicia tube 7580 may also be rotated in the second rotating direction 1162 and be moved toward the distal end 101 of the medical injection system 100 based on the first thread direction.

In some implementations, when the control knob 542 is rotated in the first rotating direction 1161, the indicia tube 7580 may also be rotated in the first rotating direction 1161 and be moved toward the distal end 101 of the medical injection system 100 based on a second thread direction opposite to the first thread direction. In some implementations, when the control knob 542 is rotated in the second rotating direction 1162, the indicia tube 7580 may also be rotated in the second rotating direction 1162 and be moved toward the proximal end 102 of the medical injection system 100 based on the second thread direction.

In some implementations, the first thread direction may be one of a left-hand helix and a right-hand helix, and the second thread direction may be the other one of the left-hand helix and the right-hand helix.

In some implementations, the indicia tube 7580 may be moved toward the proximal end 102 of the medical injection system 100 and rotated in the first rotating direction 1161 when the dose of the drug or the medical fluid is adjusted to be increased, for example, by rotating the control knob 542 in the first rotating direction 1161. With reference to FIG. 8, the dose plate 7560 may also be moved toward the proximal end 102, since the dose plate 7560 may be abutted against the indicia tube 7580. In addition, with reference to FIG. 9, the driver sleeve 7540 may also be moved toward the proximal end 102, since the driver sleeve 7540 may be abutted against the dose plate 7560. Furthermore, the indicia tube 7580 may be moved toward the distal end 101 of the medical injection system 100 and rotated in the second rotating direction 1162, for example, when the dose of the drug or the medical fluid is adjusted to be decreased by rotating the control knob 542 in the second rotating direction 1162.

In other implementations, the indicia tube 7580 may be moved toward the distal end 101 of the medical injection system 100 and rotated in the first rotating direction. 1161, for example, when the dose of the drug or the medical fluid is adjusted to be decreased by rotating the control knob 542 in the first rotating direction 1161. Furthermore, the indicia tube 7580 may be moved toward the proximal end 102 of the medical injection system 100 and rotated in the second rotating direction 1162, for example, when the dose of the drug or the medical fluid is, adjusted to be increased by rotating the control knob 542 in the second rotating direction 1162.

In some implementations, when the control knob 542 is rotated to adjust the dose, the sleeve holder 543 may remain unrotated and stay in place due to no engagement between the control knob 542 and the sleeve holder 543. Thus, the driver sleeve 7540, the drive 7510, the locking nut 7520, the rotating ring 7530 and the lead screw 7500 may also remain unrotated and stay in place.

Figure 14:
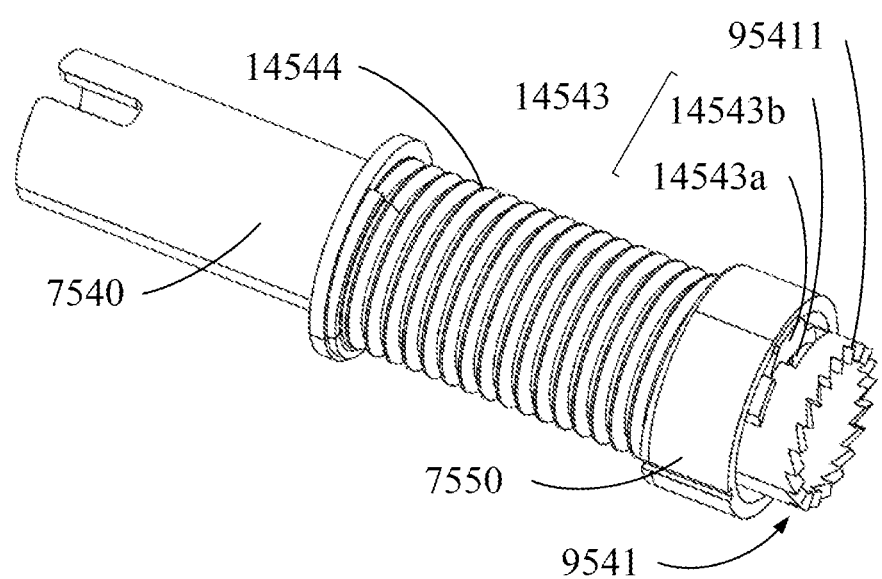
FIG. 14 is a perspective view of a combination of the drive sleeve and the screw nut of the medical injection system, in accordance with an embodiment of the present disclosure.

FIG. 14 is a perspective view of a combination of the driver sleeve 7540 and the screw nut 7550 of the medical injection system, in accordance with an embodiment of the present disclosure. In some implementations the driver sleeve 7540 may further include a position structure 14543 and a sleeve thread 14544.

In some implementations, the sleeve thread 14544 of the driver sleeve 7540 may engage with the screw nut 7550. Thus, the screw nut 7550 may be rotatable on the sleeve thread 14544 of the driver sleeve 7540. In some implementations, the position structure 14543 may be located between the sleeve thread 14544 and the sleeve teeth 95411 to define an initial position of the screw nut 7550.

In some implementations, the position structure 14543 may further include a position protrusion 14543*a* and a plurality of position notches 14543*b* in some implementations, the position protrusion 14543*a* may be outwardly protruded from an outer surface of the first sleeve end 9541 of the driver sleeve 7540 and located near the sleeve thread 14544. In some implementations, the position notches 14543*b* may be coupled to the position protrusion 14543*a*.

Figure 15:
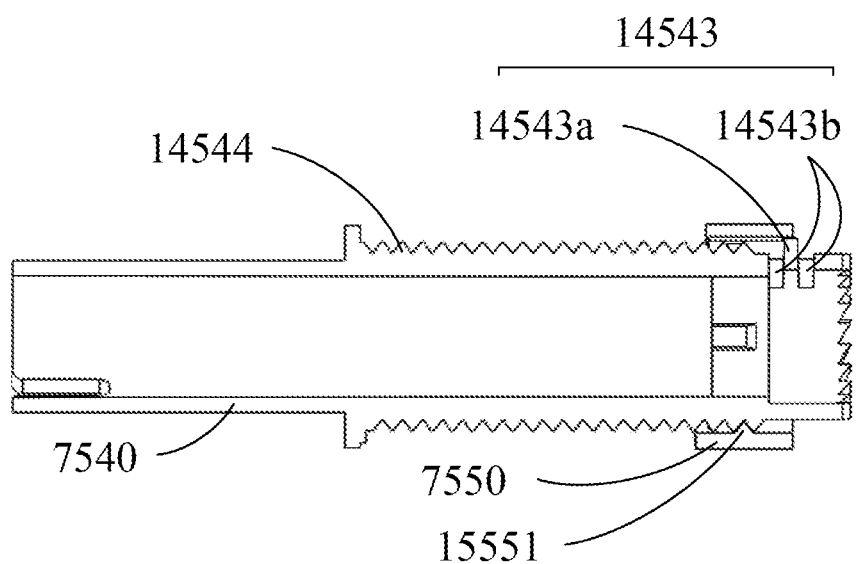
FIG. 15 is a cross-sectional view of a combination of the driver sleeve and the screw nut of the medical injection system, in accordance with an embodiment of the present disclosure.

FIG. 15 is a cross-sectional view of a combination of the driver sleeve 7540 and the screw nut 7550 of the medical injection system, in accordance with an embodiment, of the present disclosure. The direction of the cross-sectional view shown in FIG. 15 may be different from the directions of the cross-sectional views shown in FIG. 2 and FIG. 8. Thus, the structure of the driver sleeve 7540 and the screw nut 7550 shown in FIG. 15 may be slightly different from those shown in FIG. 2 and FIG. 8. In some implementations, the screw nut 7550 may include a nut thread 15551 inwardly protruded from an inner surface of the screw nut 7550.

In some implementations, the nut thread 15551 may engage with the sleeve thread 14544, such that the screw nut 7550 may be rotatable, on the driver sleeve 7540 by an engagement between the nut thread 15551 and the sleeve thread 14544. In addition, in some implementations, the number of the position notches 14543*b* may be equal to two, so the position protrusion 14543*a* may be sandwiched between the position notches 14543*b*.

Figure 16:
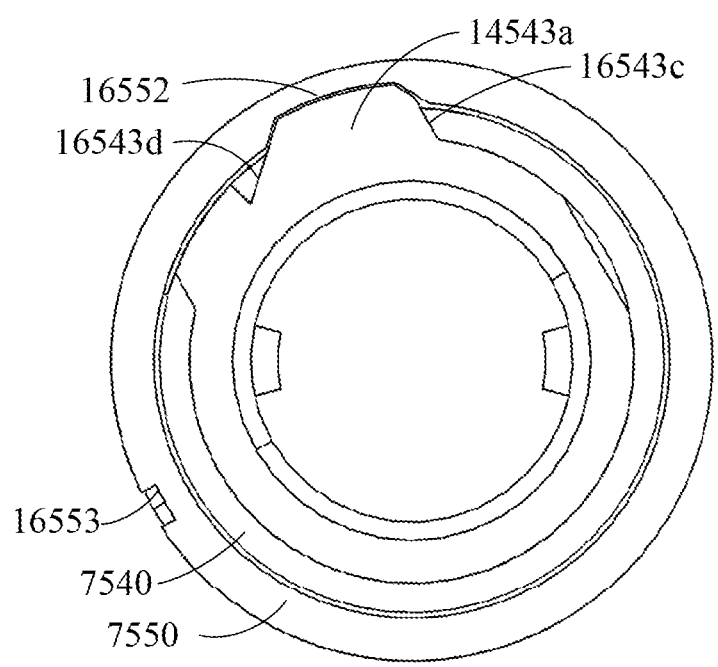
FIG. 16 is another cross-sectional view of a combination of the driver sleeve and the screw nut of the medical injection system, in accordance with an embodiment of the present disclosure.

FIG. 16 is another cross-sectional view of a combination of the driver sleeve 7540 and the screw nut 7550 of the medical injection system, accordance with an embodiment of the present disclosure. The direction of the cross-sectional view shown in FIG. 16 may be perpendicular to the direction of the cross-sectional view shown in FIG. 15. In some implementations the screw nut 7550 may include a nut recess 16552 concaved from an inner surface of the screw nut 7550 and a nut notch 16553 concaved from an outer surface of the screw nut 7550.

In some implementations, the nut recess 16552 may engage with the position protrusion 14543*a* (e.g., as shown in FIGS. 14 and 15) for defining the initial position of the screw nut 7550. In some implementations, the shape of the position protrusion 14543*a* may be similar to the shape of the nut recess 16552. Thus, the driver sleeve 7540 may be able to insert into the screw nut 7550 when the nut recess 16552 corresponds to the position protrusion 14543*a*.

In some implementations, the position protrusion 14543*a* may include a fifth inclined surface 16543*c* having a fifth slope and a sixth inclined surface 16543*d* having a sixth slope that may be different from the fifth slope. In some implementations, the fifth slope and the sixth slope may be calculated based on the outer surface of the first sleeve end 9541 of the driver sleeve 7540. Thus, the sixth slope may be less than the fifth slope. In some implementations, the nut recess 16552 may further include a seventh inclined surface (not shown) having a seventh slope and an eighth inclined surface (not shown) having, an eighth slope. In some implementations, the fifth slope may be similar to the seventh slope and the sixth slope may be similar to the eighth slope. Thus, theposition protrusion 14543*a* may engage closely with the nut recess 16552.

In some implementations, with reference to FIG. 15 and FIG. 16, after the driver sleeve 7540 is inserted into the screw nut 7550 the screw nut 7550 may stop at the initial position when the nut thread 15551 is in contact with the sleeve thread 14544. When the screw nut 7550 is located at the initial position, the screw nut 7550 may partially cover the position protrusion 14543*a*, in other words, a part of the position protrusion 14543*a* may be, uncovered by the screw nut 7550 and exposed from the screw nut 7550.

In some implementations, when the screw nut 7550 is located at the initial position, the position protrusion 14543*a* may be partially engaged with the nut recess 16552. Thus, it may be not easy to rotate the screw nut 7550 on the driver sleeve 7540 due to the partial engagement between the position protrusion 14543*a* and the nut recess 16552. However, in some implementations, the sixth slope and the eighth slope may be low enough for the eight inclined surface to press the sixth inclined surface 16543*d* down. In some implementations, since the position protrusion 14543*a* is sandwiched between the position notches 14543*b*, the position protrusion 14543*a* may be flexible. Thus, when the screw 7550 rotates to move away from the position protrusion 14543*a*, the press generated by the nut recess 16552 or the inner surface of the screw nut 7550 may release and the position protrusion 14543*a* may self-recover back. In other words, when a force (e.g., generated by a user) is exerted for rotating the screw nut 7550, the nut recess 16552 may still be able to overcome an interference of the position protrusion 14543*a*. Then, the screw nut 7550 may start rotating on the driver sleeve 7540 and moving away from the initial position near the position protrusion 14543*a*. In some implementations, when there is no position structure 14543 on the screw nut 7550, the screw nut 7550 may rotate arbitrarily. Thus, the screw nut 7550 may not have an initial position at which the screw nut 7550 may be fixed before the medical injection system 100 is used.

With further reference to FIG. 7 and FIG. 12, in some implementations, the nut notch 16553 may engage with the indicia tube 7580. Thus, when the indicia tube 7580 is rotated by the control knob 542 in one of the first rotation direction 1611 and the second rotation direction 1612 to move toward the distal end 101 of the medical injection system 100, the screw nut 7550 may also be rotated in the one of the first rotation direction 1611 and the second rotation direction 1612 to most toward the distal end 101. In addition, when the indicia tube 7580 is rotated by the control knob 542 in the other one of the first rotation direction 1611 and the second rotation direction 1612 to move toward the proximal end 102 of the medical injection system 100, the screw nut 7550 may also be rotated in the other one of the first rotation direction 1611 and the second rotation direction 1612 to move toward the proximal end 102. In addition, when the driver sleeve 7540 is rotated by the control button 541 in one of the first rotation direction 1611 and the second rotation direction 1612 for injecting the drug or the medical fluid, the indicia tube 7580 may also be rotated in the one of the first rotation direction 1611 and the second rotation direction 1612. In some implementations, the screw nut 7550 sandwiched between the driver sleeve 7540 and the indicia tube 7580 may remain unrotated when the driver sleeve 7540 and the indicia tube 7580 are rotated together. Thus, the rotation of the screw nut 7550 may be used to control a maximum dose by the control knob 542.

The embodiments shown and described above are only examples. Many details are often found in the art. Therefore, many such details are neither shown nor described. Even though numerous characteristics and advantages of the present disclosure have been set forth in the foregoing description, together with details of the structure and function of the present disclosure, the present disclosure is illustrative only, and changes may be made in the detail. It will therefore be appreciated that the embodiment described above may be modified within the scope of the claims.

What is claimed is:

1. A medical injection system, comprising:
   an injection module, comprising:
      a lead screw movable along an axial line of the medical injection system;
      a drive configured to partially accommodate the lead screw and to be rotatable together with the lead screw;
      a driver sleeve configured to partially accommodate the driver and to have a first sleeve end facing a distal end of the medical injection system, the first sleeve end having a plurality of sleeve teeth;
      a dose plate including a first plate end facing the distal end, a second plate end facing a proximal end of the medical injection system, and a side surface located between the first plate end and the second plate end, the second plate end having a plurality of plate teeth corresponding to the plurality of sleeve teeth, the side surface having a surface tooth; and
      an indicia tube configured to accommodate the driver sleeve and the dose plate and to have a plurality of tube concaves near a first tube end facing the distal end, wherein the surface tooth of the dose plate corresponds to one of the plurality of tube concaves; and
   a cartridge module coupled to the injection module, wherein the lead screw is configured to move along the axial line into the cartridge module.

2. The medical injection system of claim 1, wherein:
   each of the plurality of the plate teeth is engaged with one of the plurality of sleeve teeth; and
   the surface tooth is engaged with one of the plurality of tube concaves.

3. The medical injection system of claim 1, further comprising:
   a control knob rotatable in a first rotating direction and a second rotating direction and coupled to the indicia tube, wherein:
   when the control knob is rotated in the first rotating direction, each of the plurality of the plate teeth engaged with one of the plurality of sleeve teeth is rotated to engage with another one of the plurality of sleeve teeth, and
   when the control knob is rotated in the second rotating direction, the plurality of tube concaves is rotated to change an engaged target of the surface tooth from one of the plurality of tube concaves to another one of the plurality of tube concaves.

4. The medical injection system of claim 3, wherein:
   a first sound is generated by the plurality of the plate teeth and the plurality of sleeve teeth for indicating the first rotating direction, and
   a second sound different from the first sound is generated by the surface tooth and the plurality of tube concaves for indicating the second rotating direction.

5. The medical injection system of claim 3, wherein:
   when the control knob is rotated in the first rotating direction, the indicia tube is moved toward the proximal end of the medical injection system, and
   when the control knob is rotated in the second rotating direction, the indicia tube is moved toward the distal end of the medical injection system.

6. The Medical injection system of claim 3, wherein:
   the surface tooth includes a first inclined surface having a first slope and a second inclined surface having a second slope different from the first slope,
   the first inclined surface is configured to lock the surface tooth on the one of the plurality of rube concaves for rotating, the dose plate in a third rotating, direction by the indicia tube, and
   the surface tooth is moveable between the plurality of tube concaves through the second inclined surface without rotating the dose plate during a rotation of the indicia tube.

7. The medical injection system of claim 6, wherein:
   the surface tooth is locked on the one of the plurality of tube concaves to rotate the dose plate by the indicia tube when the control knob is rotated in the first rotating direction, and
   the surface tooth remains unrotated and the plurality of tube concaves is rotated b surrounding the surface tooth when the control knob is rotated in the second rotating direction.

8. The medical injection system of claim 6, Wherein the third rotating direction is identical to one of the first rotating direction and the second rotating direction.

9. The medical injection system of claim 1, wherein:
   when the control knob rotates the indicia tube in a first rotating direction, the dose plate is rotated by the indicia tube and the driver sleeve remains unrotated, and
   when the control knob rotates the indicia tube in a second rotating direction different from the first rotating direction, the dose plate and the driver sleeve remain unrotated.

10. The medical injection system of claim 9, wherein:
    when the control knob rotates the indicia tube in the first rotating direction, a first relative rotation between the dose plate and the indicia tube is caused to generate a first sound, and
    when the control knob rotates the indicia tube in the second rotating direction, a second relative rotation between the dose plate and the driver sleeve is caused to generate a second sound.

11. The medical injection system of claim 1, further comprising a screw nut engaged with the driver sleeve.

12. The medical injection system of claim 11, wherein the driver sleeve further comprises:
- a sleeve thread engaged with the screw nut, wherein the screw nut is rotatable over the sleeve thread; and
- a position structure located between the sleeve thread and the plurality of sleeve teeth and configured to define an initial position of the screw nut.

13. The medical injection system of claim 12, wherein the position structure further comprises:
- a position protrusion outwardly protruded near the sleeve thread; and
- a plurality of position notches coupled to the position protrusion, wherein the position protrusion is sandwiched between at least two of the plurality of position notches.

14. The medical injection system of claim 13, wherein the screw nut further comprises:
- a nut thread engaged with the sleeve thread to rotate the screw nut over the drive sleeve; and
- a nut recess engaged with the position protrusion for defining the initial position.

15. The medical injection system of claim 1, wherein the indicia tube further comprises:
- an internal protrusion surrounding an inner surface of the indicia tube and located near the first tube end, wherein:
  - the internal protrusion is in contact with the first plate end of the dose plate, and
  - the dose plate is located between the internal protrusion and the second rube end facing the proximal end.

16. A medical injection system, comprising:
an injection module, comprising:
- a lead screw movable along, an axial line of the medical injection system;
- a driver sleeve configured to partially accommodate the lead screw and to have a first sleeve end facing a distal end of the medical injection system, the first sleeve end having a plurality of sleeve teeth;
- a dose plate including a first plate end facing the distal end, a second plate end facing a proximal end of the medical injection system, and a side surface located between the first plate end and the second plate end, the second plate end having a plurality of plate teeth corresponding to the plurality of sleeve teeth, the side surface having a surface tooth; and
- an indicia tube configured to accommodate the driver sleeve and the dose plate and to have a plurality of tube concaves near a first tube end facing the distal end, the surface tooth of the dose plate corresponding to one of the plurality of tube concaves and including a first inclined surface having a first slope and a second inclined surface having a second slope different from the first slope; and
a cartridge module coupled to the injection module, wherein the lead screw is configured to move along the axial line into the cartridge module.

* * * * *